(12) United States Patent  
Webb et al.

(10) Patent No.: US 8,049,883 B2  
(45) Date of Patent: Nov. 1, 2011

(54) WAVELENGTH TRACKER FOR SWEPT WAVELENGTH SENSOR INTERROGATION SYSTEM

(75) Inventors: Michael B. Webb, Lindley, NY (US); Qi Wu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 456 days.

(21) Appl. No.: 12/394,109

(22) Filed: Feb. 27, 2009

(65) Prior Publication Data

US 2010/0296089 A1 Nov. 25, 2010

(51) Int. Cl.  
*G01J 3/28* (2006.01)

(52) U.S. Cl. ............... 356/326; 356/308; 356/328

(58) Field of Classification Search .......... 356/326, 356/328  
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 6,429,022 B1 | 8/2002 | Kunz et al. | 436/164 |
| 6,785,433 B2 | 8/2004 | Tiefenthaler | 385/12 |
| 7,217,951 B2 | 5/2007 | Krishna et al. | 257/21 |
| 7,310,153 B2 | 12/2007 | Kiesel et al. | 356/519 |
| 7,355,162 B2 | 4/2008 | Sidorin | 250/227.11 |
| 2006/0050271 A1* | 3/2006 | McDonald | 356/328 |
| 2007/0020689 A1 | 1/2007 | Caracci et al. | 435/7.1 |
| 2008/0204760 A1 | 8/2008 | Gollier et al. | 356/484 |
| 2008/0315078 A1 | 12/2008 | Ono | 250/238 |

FOREIGN PATENT DOCUMENTS

| | | |
|---|---|---|
| WO | WO 01/16569 | 3/2001 |
| WO | WO 2004/092730 | 10/2004 |

OTHER PUBLICATIONS

Ph.M. Nellen, et al., "Integrated Optical Input Grating Couplers as Biochemical Sensors", *Sensors and Actuators*, 1988, vol. 15, pp. 285-295.  
T.C. Black, "Physics 102 Lab 8: Measuring Wavelengths with a Diffraction Grating", Spring 2005.  
T. Farrell, et al., "Tunable Laser Technology for Sensing Applications", *Physics and Application of Optoelectronic Devices, Proceedings of SPIE*, vol. 5594, pp. 66-80, 2004.  
The Corning Epic® System, New Targets. New Information, Overview Brochure, 2007.  
Epic® System presentation, A. Frutos, 2006.

* cited by examiner

*Primary Examiner* — F. L. Evans  
(74) *Attorney, Agent, or Firm* — John L. Haack; Thomas Ryan

(57) ABSTRACT

A swept wavelength interrogation system includes a tunable light source for outputting a light beam that is tunable over a range of wavelengths and an optical reader head for distributing the light beam among a plurality of sensors and for measuring response spectra from the sensors. A wavelength-tracking device measures centroid wavelengths of the light beam. A processor calculates a centroid wavelength of the response spectra from the sensors based on the measured centroid wavelengths of the light beam.

21 Claims, 4 Drawing Sheets

US 8,049,883 B2

WAVELENGTH TRACKER FOR SWEPT WAVELENGTH SENSOR INTERROGATION SYSTEM

The entire disclosure of any publication, patent, or patent document mentioned herein is incorporated by reference.

BACKGROUND

The disclosure relates to label-free screening technologies for detecting molecular interactions, particularly swept wavelength interrogation systems of resonant waveguide sensors, and to wavelength tracking systems for such interrogation systems.

SUMMARY

The disclosure provides a label-free biosensor apparatus and methods thereof, including a wavelength tracker for swept wavelength sensor interrogation.

DETAILED DESCRIPTION

Figure 1:
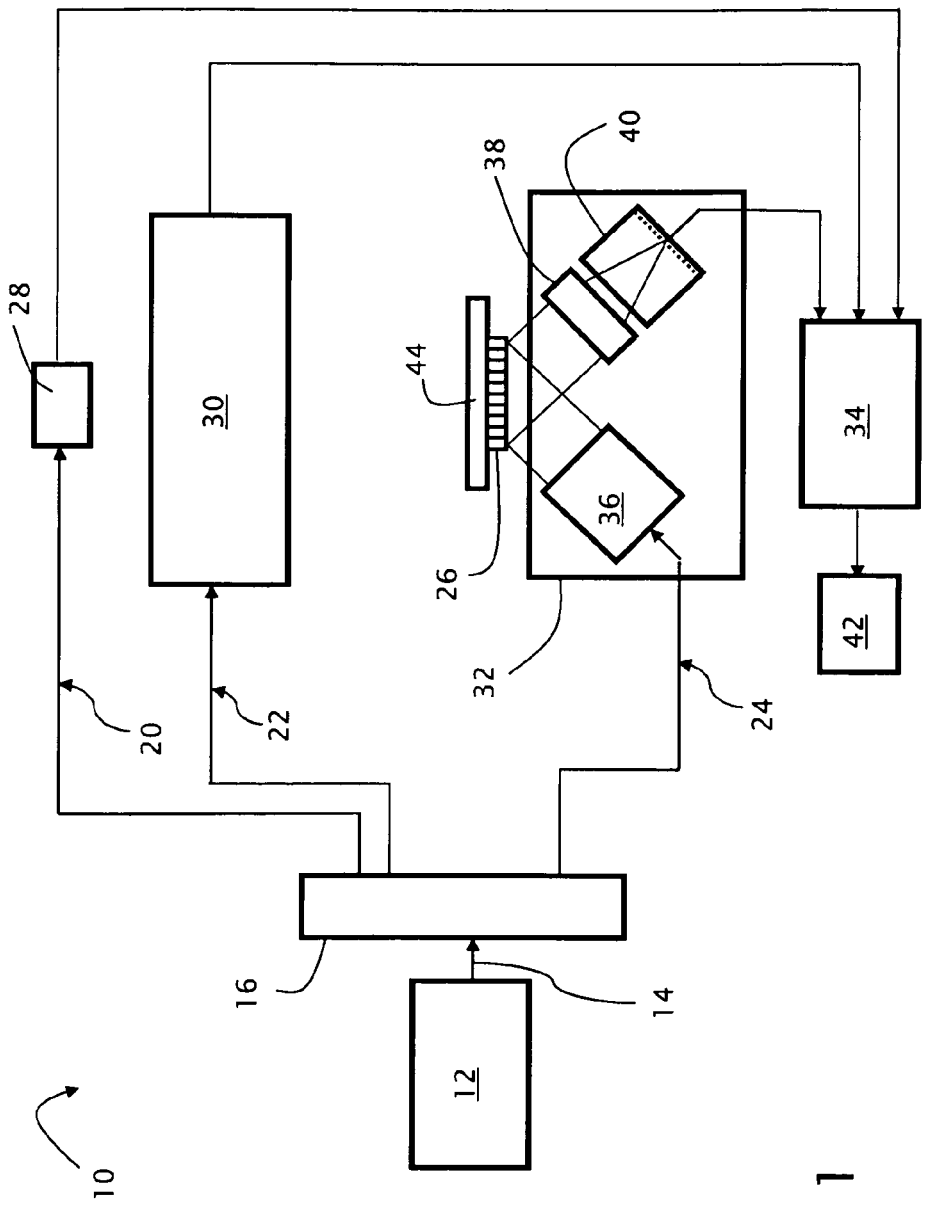
FIG. 1 is a block diagram of a swept wavelength sensor interrogation system arranged with a wavelength-tracking device, in embodiments of the disclosure.

Molecular reactions, including bio-molecular reactions and biological interactions, can be studied in high-throughput automated assays by optical interrogation techniques based on the detection of minute refractive index changes associated with variations among molecular species, such as the bonding of receptor molecules to analyte molecules. The sensors generally include resonant waveguides with grating couplers. Analyte molecules within the evanescent field of the waveguides produce small changes in the effective refractive index of the waveguides, which manifests itself as corresponding changes in the resonant conditions of the sensor's waveguides.

The sensors, which can be grouped in an array for processing a large number of analyte samples, can be interrogated by exposing the sensors to a range of wavelengths and measuring the spectral response profile of the returning light. For example, the sensors can be exposed to light from a broadband source and a spectrometer can be used to analyze the reflectivity spectra from each sensor. A centroid wavelength can be determined for each measured sample as a basis for making comparisons among the samples.

Instead of exposing a sensor to a broadband source and sorting the energy content of the reflected spectra, the sensor can be exposed to a succession of different wavelengths, referred to as "swept wavelength" interrogation, and the reflected energy of each of the different wavelengths can be measured for performing a similar spectral analysis. Although more demands are made on the light source and the different wavelengths must be precisely measured, the swept wavelength interrogation technique requires only simple optical power sensors to quantify the response spectra of the sensors instead of requiring spectrometers to both distinguish among the wavelengths and determine the energy content of the distinguished wavelengths.

The accuracy with which a centroid wavelength of the sensor response spectra can be determined for the sensor resonance depends inter alia upon the accuracy at which the relative reflectivity of the sensors can be measured and the accuracy at which the interrogating wavelengths can be measured. The light sources for practicing swept wavelength techniques are typically tunable external cavity lasers capable of outputting narrow linewidth beams over a range of wavelengths. The associated instruments for measuring the individual wavelengths output from the tunable lasers typically include both a two-arm interferometer (e.g., a Mach-Zehnder interferometer) for decoding the instantaneous wavelength and an athermalized etalon as a reference.

Preferably, the centroid wavelength of the sensor resonance can be based on the centroid wavelengths of the light beam and the energy contents of the spectrally shifted light beam returning from the sensor. Both the centroid wavelengths of the light beam and the centroid wavelength of the sensor resonance represent a weighted mean of a plurality of considered wavelengths weighted according to optical energy content of the considered wavelengths. The considered wavelengths used to measure the centroid wavelength of the light beam are the wavelengths that form the linewidth of the light beam. The considered wavelengths used to measure the centroid wavelength of the sensor resonance are the measured centroid wavelengths of the light beam. Regardless of which wavelengths are considered for which centroid, both centroids are similarly defined in terms of wavelength and optical energy as the wavelength about which the spectral optical energy is balanced.

Both the tunable external-cavity lasers themselves and their associated interferometric wavelength measuring systems tend to be expensive and difficult to maintain to required precision. For example, care must be taken to maintain the lasing cavities of the tunable lasers in a particular condition to support a range of tuning while avoiding mode hop. The need for precise wavelength measurements of less than one picometer (pm) and preferably about 0.1 pm for a sampling size of 1,000 different wavelength measurements necessitates even further narrowed linewidth interrogating beams, for example, beam linewidths of less than about one femtometer (fm) to interferometrically resolve the interrogating beams to the required precision. While the narrow linewidths are necessary for interferometric resolution, the correspondingly long coherence length of the interrogating beams subjects the measurements to unwanted interferometric effects referred to as "speckle". The speckle effects, which can disturb propagations of light to and from the sensors, vary between conditions of constructive and destructive interference in response to the tuning of the interrogating beams through the progression of wavelengths.

In embodiments, the disclosure provides an apparatus and method which can expand the linewidth of interrogating beams used in a swept wavelength interrogation system for measuring spectral responses of sensor arrays, including biosensors. For example, interrogating beam linewidths of ten picometers or more up to and including the resonance width of the sensors are contemplated despite requirements for measuring the interrogating beam wavelengths to a precision much less than ten picometers. A shortened coherence length of the expanded linewidth beam avoids unintended interference effects that can distort measurements of the returning optical power of from the sensors. In embodiments, low cost and easy to maintain light sources can be used for swept wavelength interrogation techniques while resolving comparisons between sensor responses to desired or even improved accuracy.

In embodiments, the wavelength-shifted interrogation beam should have as narrow a linewidth as possible to distinguish among the returning energy contents of closely spaced wavelengths. For the purpose of interrogating resonant sensors with a sensitivity to refractive index changes on the order of $10^{-6}$, the interrogating beam wavelengths have been required to be known with a precision of less than one picometer at a sampling size of 1,000 different wavelengths and have had linewidths measured in femtometers. However, in contrast to other spectroscopic applications that may require measuring the entire response spectra of the resonant sensors, many resonant sensor interrogations require only a measure of the centroid wavelength of the sensor response spectra. As such, it is only the different centroid wavelengths of the interrogating beam that must be known with high precision, while the linewidth over which the sensor resonance is sampled by each wavelength of the interrogating beam can be much wider. However, the centroid wavelengths of the interrogation beam should be defined compatibly with the centroid wavelengths of sensor resonance so that the enlarged linewidth of the interrogation beam does not affect the accuracy with which the centroid wavelengths of sensor resonance are determined.

As the interrogation beam linewidth more closely approaches the resonance width of the sensors, the interaction of the spectrally shifted profiles of the interrogating beam with the spectral response profiles of the resonant sensors transforms from discrete poling to a convolution function. The interrogation beam can have a linewidth that tests the sensor response through overlapping ranges of wavelength. The centroid wavelength of the sensor spectral response can be found from the returning energy content weighted sum of the centroid wavelengths of the interrogating beam. As such, care is exercised to avoid changes in the spectral profiles of the interrogation beam between the spectral profiles at which the beam is measured and the spectral profiles at which the beam interrogates the sensors, especially as such changes may evolve over the tuning range.

In embodiments, the disclosure provides a swept wavelength interrogation system including a tunable light source for outputting a light beam that is tunable over a range of wavelengths and an optical reader head for distributing the light beam among a plurality of sensors, i.e., as one or more interrogating beams, and for measuring response spectra from the sensors. In addition, a wavelength-tracking device measures centroid wavelengths of the light beam with a given precision. The light beam can have a linewidth that exceeds the given precision with which the centroid wavelengths are measured.

In embodiments, the linewidth of the light beam can exceed the given precision with which the centroid wavelengths are measured by a factor of about 10 or more. For example, the linewidth of the interrogating beams can be about 10 picometers or more while the given precision with which the centroid wavelengths are measured can be less than about one picometer. In addition, the wavelengths of the light beam can be spaced by a nominal step size and the linewidth of the interrogation beams can exceed the nominal step size. The sensors generally have a defined resonance width and the linewidth of the light beam can be more than about five percent of the resonance width of the sensors up to and including the resonance width of the sensors.

In embodiments, the tunable light source can be, for example, a multi-longitudinal mode laser that can simultaneously oscillate in a multitude of different longitudinal modes for enlarging the linewidth of the light beam. In embodiments, the multi-longitudinal mode laser can preferably simultaneously oscillate in 100 or more longitudinal modes to reduce the influence of mode hopping.

In embodiments, the interrogation system can include a processor for determining centroid wavelengths of the response spectra. The centroid wavelengths of the sensor response spectra can be determined within a measurement error of about 100 femtometers or less based on the measurement error with which the centroid wavelengths of the light beam are measured of about 0.3 picometers or less.

In embodiments, the disclosure can provide a wavelength tracking apparatus of a swept wavelength sensor interrogation system for measuring a centroid wavelength of sensor resonance. A dispersive optic alters a spatial position of the light beam as a function of the wavelength of the light beam. A spatially sensitive sensor system measures optical power as a function of the spatial position of the light beam. A processor converts optical power measured with respect to the spatial position of the light beam into a measure of a centroid wavelength of the light beam according to an algorithm compatible with an algorithm for determining the centroid wavelength of sensor resonance.

In embodiments, the centroid wavelength of sensor resonance can be based on the centroid wavelengths of the light beam and the energy contents of the spectrally shifted light beam returning from the sensor. Both the centroid wavelengths of the light beam and the centroid wavelength of sensor resonance represent a weighted mean of a plurality of considered wavelengths weighted according to optical energy content of the considered wavelengths. The considered wavelengths for determining the centroid wavelength of sensor resonance are the measured centroid wavelengths of the light beam.

In embodiments, the disclosure provides a method of interrogating an array of sensors for measuring sensor response to analytes proximate to the sensors. A light source is tuned for outputting a light beam through a range of wavelengths. The light beam is split between a beam-monitoring pathway and a sensor-interrogating pathway. Along the beam-monitoring pathway, centroid wavelengths of the light beam are measured. Along the sensor-interrogating pathway, optical power of the light beam is distributed among the array of sensors, for example, as one or more interrogating beams, and optical power returning from the array of sensors is measured. Centroid wavelengths of response spectra from the sensors are determined based on the measured centroid wavelengths of the light beam and on the measured optical power returning from the array of sensors.

In embodiments, both the centroid wavelengths of the light beam and the centroid wavelengths of the response spectra from the sensors represent a weighted mean of a plurality of considered wavelengths weighted according to optical energy content of the considered wavelengths. The centroid wavelengths of the light beam are measured with a given precision and the light beam has a linewidth that can exceed the given precision with which the centroid wavelengths of the light beam are measured.

During tuning, the light beam can be output as multi-longitudinal mode beam containing at least about 100 different longitudinal modes that can vary in modal content over the range of wavelengths of the light beam. In the course of measuring the centroid wavelengths of the light beam, a spatial position of the light beam can be altered as a function of the wavelength of the light beam, the optical power can be measured in reference to the spatial position of the light beam, and the optical power measured in reference to the spatial position of the light beam can be converted into a measure of the centroid wavelength of the light beam.

Referring to the Figures, FIG. 1 shows a swept wavelength interrogation system 10 which is useful for performing highly sensitive time-constrained assays. A tunable light source 12 of the interrogation system 10 includes a tuning range for outputting a light beam 14 that is tunable over a range of wavelengths. For temporally distinguishing the wavelengths, the tunable light source 12 can be stepped through the range of wavelengths with a fixed interval for each step or, more preferably, the tunable light source 12 can be continuously tuned through the range of wavelengths, which are sampled at discrete intervals.

The tunable light source 12 is preferably a multi-longitudinal mode laser that simultaneously oscillates in a multitude of different longitudinal modes for enlarging the linewidth of the light beam 14 and for reducing the influence of mode hopping during the tuning. For these purposes, the multi-longitudinal mode laser preferably has a linewidth of ten picometers or more and preferably simultaneously oscillates in at least about 100 or more longitudinal modes. The tunable light source 12 can preferably have a linewidth of about 100 picometers or more up to and including the resonance width of the sensors subject to interrogation (e.g., approximately one nanometer). Multi-longitudinal mode lasers feature broader tuning ranges because the significance of mode hops is diminished by the number of longitudinal modes within linewidth of each of the output beams. Tunable multi-longitudinal mode lasers appropriate for these purposes are available from, for example, Superlum Diodes, Ltd., Moscow, Russia, particularly models BS-840. Other tunable lasers, as well as high-power broadband sources with tunable filters, can also be used. The optical power of the tunable light source can be further enhanced by undergoing optical amplification.

A three-way beamsplitter (1×3 splitter) 16 divides the light beam 14 among three optical pathways, such as a power-monitoring pathway 20, a wavelength-monitoring pathway 22, and a sensor-interrogating pathway 24. An array of sensors 26, which can be in the form of a sensor-embedded microplate, can be arranged for communication with a set of analytes (not shown), which are subject to test. The light beam 14 can be conducted along respective portions of the three optical pathways 20, 22, and 24 in various ways, including, for example, by fiber optics, integrated waveguides, or bulk optics.

Along the power-monitoring pathway 20, a power-tracking device 28, which can include a photodiode, monitors changes in the optical power of the light beam 14 emitted by the tunable light source 12. Along the wavelength-monitoring pathway 22, a wavelength-tracking device 30 monitors changes in the centroid wavelengths of the interrogating beams 14. The wavelength-tracking device 30 accommodates light beam linewidths that exceed the precision with which the centroid wavelengths can be measured. Along the sensor-interrogating pathway 24, an optical reader head 32 optically interrogates the array of sensors 26 for monitoring changes within or among the test analytes.

A processor 34 can be, for example, a programmable computer, a microprocessor, a field programmable gate array (FPGA), or like device. The processor 34 can communicate with the tunable light source 12, the power-tracking device 28, the wavelength-tracking device 30, and the optical reader head 32 for collecting information regarding the instant power of the light beam 14, the instant centroid wavelength of the light beam 14, and the instant responses of the array of sensors over the range of wavelengths of the light beam 14 for quantifying the monitored changes in or among the test analytes. An output device 42, which can also take a variety of forms, such as a display, printer, recorder, or communications node, receives the processed output relating to the condition of the sensors 26. Device 42 can further interpret their condition, or other information about or derived from the components of the interrogation system 10 for purposes of communicating this information beyond the interrogation system 10.

In embodiments, the optical reader head 32 can take a number of forms for directing the light beam 14 to and from the array of sensors 26, and for monitoring the returning light for changes relating to the instant conditions of the sensors 26. As shown, the optical reader head 32 can include an illuminator 36 for evenly distributing the light beam 14 over the array of sensors 26, an imager 38 for collecting the returning light from the array of sensors 26 as images of the sensors 26 themselves, and a detector 40 for capturing the images of the sensors 26. The detector 40, which can include an array of charge-coupled devices (CCD), receives the images of the sensors 26 in spatially distinguished positions and detects the intensities with which each of the sensor images is formed.

Although depicted as operating in a grazing incidence mode where the light beam 14 travels to and from the array of sensors 26 through different angular ranges, the optical reader head 32 can be arranged so that the light beam 14 shares overlapping paths to and from the array of sensors at normal or near normal incidence. A number of differently configured optical reader heads that might be used in the practice of this invention are disclosed in co-assigned US Patent Application Publication No. 2008/0204760 entitled "Swept Wavelength Imaging Optical Interrogation System and Method for Using Same." Non-imaging optical reading heads, where individual detectors (e.g., photodetectors) are related to the sensors, can also be used.

The array of sensors 26 can be associated with and, for example, be preferably embedded within the wells of a microplate 44 for subjecting the analytes to screening. Examples of such microplates are disclosed in co-assigned US Patent Application Publication No. 2007/0020689 entitled "Label-Free High Throughput Biomolecular Screening System and Method." Such microplates are commercially available from Corning, Inc. under the EPIC® brand, such as the SBS-standard 384-well microplate.

The individual sensors 26 can be, for example, resonant sensors containing waveguide grating couplers and arranged for detecting minute changes in refractive index, preferably about $10^{-6}$ changes or less, within the waveguide structure of the sensors 26. The refractive index changes are evident in the resonant spectral response of the sensors 26.

For each wavelength of the light beam 14, the processor 34 receives data concerning a) the optical power of the light beam 14 from the power-tracking device 28, b) the centroid wavelength of the light beam 14 from the wavelength-tracking device 30, and c) the returning optical power associated with each of the sensors 26 from the optical reader head 32.

The data assembled over the tuning range can be used to compute the centroid wavelength of the responses from the individual sensors 26. The general computation according to an algorithm, a computational form of the centroid wavelength $C_k$ for a $k^{th}$ sensor 26, is:

$$C_k = \frac{\sum_{i=1}^{N} \lambda_i Y_i}{\sum_{i=1}^{N} Y_i}$$

where $C_k$ is the centroid wavelength for a $k^{th}$ sensor 26, N is the number of wavelengths of the light beam 14, $\lambda_i$ is the centroid wavelength of an $i^{th}$ wavelength, and $Y_i$ is the normalized strength of the response of the $k^{th}$ sensor 26 to the $i^{th}$ wavelength. The normalized strength $Y_i$ is computed as the optical power returned from the $k^{th}$ sensor 26 as percentage of the optical power received by the $k^{th}$ sensor 26 for the $i^{th}$ wavelength of the light beam 14. For example, the normalized strength $Y_i$ can be computed as the reflectivity of the $k^{th}$ sensor 26 to the $i^{th}$ interrogating beam 14. While the computational form of the algorithm for determining the centroid wavelength of the sensor responses can be varied, such as in the form of integral expressions, the results differ only slightly as artifacts of the forms, each providing a mathematically cogent expression of the wavelength about which the spectral energy of the response is balanced.

Measurement error $\sigma_c$ associated with this calculation for the centroid wavelength $C_k$ is contributed by two main sources: an error $\theta_\lambda$ in the measurement of the centroid wavelength $\lambda_i$ of the light beam 14, and an error $\sigma_Y$ in the measurement of the normalized strength $Y_i$ of the sensor response as given by:

$$\sigma_C = \sqrt{\sigma_\lambda + \sigma_Y}$$

Based on a Monte-Carlo simulation, assuming (a) a Lorentzian line shape with width of w and (b) the measurement error at each wavelength is uncorrelated, the error $\sigma_\lambda$ in the measurement of the centroid wavelength $\lambda_i$ of the interrogating beams 14 can be expressed as follows:

$$\sigma_\lambda = 0.94 \delta_\lambda \sqrt{\frac{\Delta}{W}} = 0.94 \frac{\delta_\lambda}{N}$$

where $\Delta$ is the wavelength step size between wavelengths of the light beam 14 and $\delta_\lambda$ is the wavelength measurement error at each step.

Considering a sensor resonance of approximately one nanometer (nm) wide, a tuning range of 10 nm, and a total N of 1,000 sampling points, the centroid error is estimated at about ten percent of the wavelength measurement error $\sigma_\lambda$. To achieve the $10^{-6}$ index sensitivity with a typical sensor 26, the total baseline noise should be less than 100 femtometers (fm). If a 30-fm portion of the noise is allocated to the centroid wavelength measurement error $\sigma_\lambda$, the wavelength measurement error $\delta_\lambda$ associated with each wavelength of the light beam 14 should be less than 0.3 picometers (pm). To achieve a similar resolution over a tuning range of 30 nm, a signal to noise ratio of approximately 100,000 to 1 is needed.

The preferred linewidth of the light beam 14 is much greater than the 0.3 pm precision with which the centroid wavelengths of the light beam 14 must be measured in the given sample. Moreover, the preferred linewidth of the light beam 14 is greater than the step size $\Delta$ between wavelengths of the light beam 14 given as 10 pm. The resulting relationship between the shifting spectra of the light beam 14 and the sensor response spectra approaches a convolution function.

In embodiments, the linewidths contemplated can be too broad to be measured by conventional interferometric techniques to the required accuracy. Generally, the free spectral range of the measuring cavity (i.e., the range over which the interference pattern repeats itself) should be considerably greater than the linewidth of the light beam to be measured but generally should be within about 100 times the required precision based on the reflectivity of the cavity surfaces. Thus, a maximum free spectral range of 10 pm would be expected for a precision of 0.1 pm. When the linewidth of the light beam 14 approaches the free spectral range of the interference cavity, contrast fades and no measurable fringes are formed. Moreover, because the linewidth is much larger than the required wavelength measurement precision, any variation of the linewidth profile can significantly affect the results.

Alternative approaches for measuring the centroid wavelength $\lambda_i$ of the light beam 14 are shown in FIGS. 2 through 5. In each instance, the centroid wavelength $\lambda_i$ is determined according to an algorithm for processing the intensity data gathered over the range of wavelengths within the linewidth of the light beam 14 of the computational form:

$$\lambda_i = \frac{\sum_{j=1}^{n} \lambda_j I_j}{\sum_{j=1}^{n} I_j}$$

where n is the number of discrete wavelengths sampled within the linewidth of the $i^{th}$ wavelength of the light beam 14, $\lambda_j$ is the $j^{th}$-measured wavelength, and $I_j$ intensity of the $j^{th}$-measured wavelength. Paralleling the algorithm for computing the centroid wavelength of sensor response spectra, a corresponding integral function can be used based on a representation of intensity as a function of wavelength. The calculations for the centroid wavelengths $\lambda_i$ of the light beam 14 for carrying out the algorithm can be explicit as programmable steps within the processor 34 or at least partially implicit from the output of detectors as described more fully below.

Figure 2:
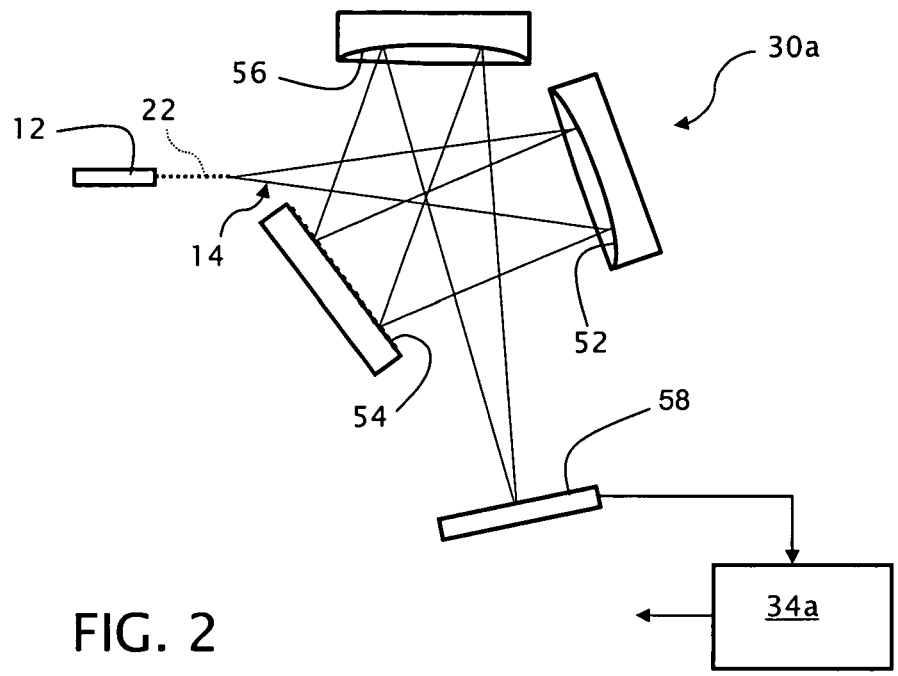
FIG. 2 shows a block diagram of a wavelength-tracking device in the swept wavelength interrogation system, in embodiments of the disclosure.

In FIG. 2, a wavelength-tracking device 30a is shown for monitoring the centroid wavelengths $\lambda_i$ of the light beam 14 along the wavelength-monitoring pathway 22 of the swept wavelength interrogation system 10. An expanding output of the light source 12, which can be controlled by optics not shown, encounters a collimating optic 52 that collimates and redirects the light beam 14 to a dispersive optic 54. Although depicted as a concave reflector, the collimating optic 52 can be formed by one or more lenses or by a combination of one or more mirrors and lenses. The dispersive optic 54, which is depicted as a reflective diffraction grating, angularly disperses the incident collimated light as a function of wavelength. The dispersive optic 54 can also take a variety of forms for accomplishing this function including, for example, a ruled grating, a replicated grating, a holographic grating, and a volume grating, any in transmissive or reflective modes. The angularly dispersed light of the light beam 14 encounters a focusing optic 56 that converts the angularly dispersed light into linearly displaced light along a focal line coincident with a spatially sensitive detector 58. The focusing optic 56 is also shown as a concave reflector but can also be formed by individual or combinations of reflective and refractive optics. Alternatively, the dispersive optic 54 can incorporate optical power in place of or in combination with the focusing optic 56, such as by adopting a curved form, a catadioptric structure, a higher-order ruling, or like modifications.

The spatially sensitive detector 58 samples the intensity of the focused light over a range of different positions along the focal line. The different positions along the focal line correspond to different wavelengths within the linewidth of the individual interrogating beams 14. At each such position that is scanned or otherwise sampled, intensity data is captured. The output of the detector 58, which is directed to a processor 34a, can be arranged to include a series of intensity related values associated with the positions from which the intensities are collected.

The detector 58 can take a variety of forms, including the form of a line-scan camera or a position-sensitive device (PSD). For example, the detector 58 can be a high-speed deep-well line-scan camera such as available from Dalsa Corporation, Waterloo, Ontario, Canada, or Basler Vision Technologies, Ahrensburg, Germany, whose output can be processed by a field programmable gate array (FPGA) in real time at a one kHz update rate. Alternatively, a position-sensitive device (PSD) can be assembled as an arrangement of silicon photodiodes that provides an analog output directly proportional to the centroid position of a light spot along the array. The analog output can be directly calibrated to wavelength, which greatly simplifies electronics and software processing and achieves nanosecond response times.

A position-sensitive device (PSD) available from On-Trak Photonics, Inc., Irvine, Calif., which includes an arrangement of silicon photodiodes together with an amplifier, outputs an analog voltage that is linearly proportional to the position of the light spot along the device. Both the position and the intensity of a light spot on the detector area can be monitored. A five-millimeter PSD array of this sort is expected to cover a tuning range of around 25 nm but can be scaled upward for covering larger tuning ranges to the required accuracy. The PSD amplifier has a gain of about $10^5$ V/A (volts per ampere) and assuming a 5 kHz detection bandwidth, a shot noise limited power detection noise as approximately 0.04 mV (millivolts). With the noise of the PSD output at about 0.06 mV, approximately 0.15 mW (milliwatts) of optical power is required.

For processing the output of a line-scan camera as described above, the processor 34a can take the form of a field programmable gate array (FPGA) in which the positions referenced to the line-scan camera can be converted to measures of wavelength, and the position-tagged intensity data from the camera can be converted where necessary into a digitally processible form for calculating the centroid wavelengths $\lambda_i$ of the interrogating beams 14. The position-related intensity data can also be processed to achieve other functionalities, such as by calculating the spectral profile of the light source 12.

Figure 3:
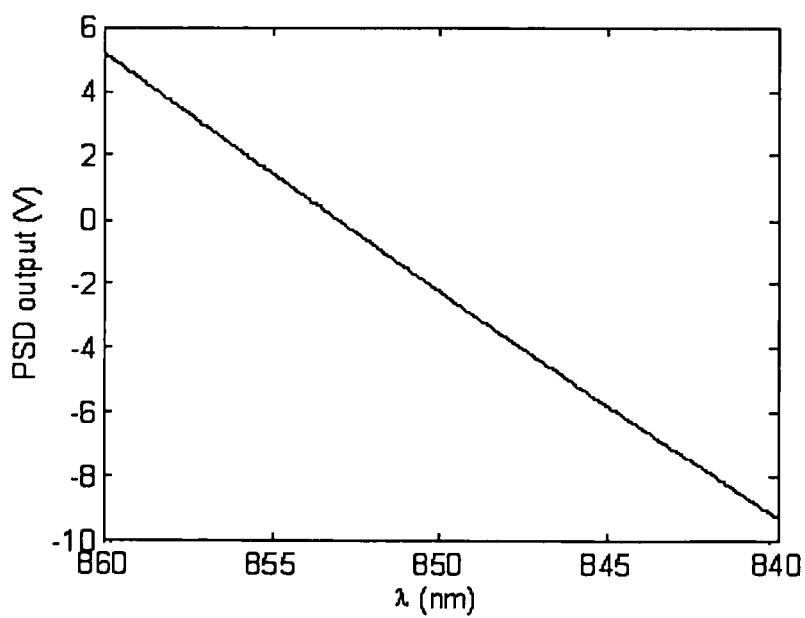
FIG. 3 is a plot of the performance of a position-sensitive device (PSD) for converting an output voltage to wavelength, in embodiments of the disclosure.
Figure 4:
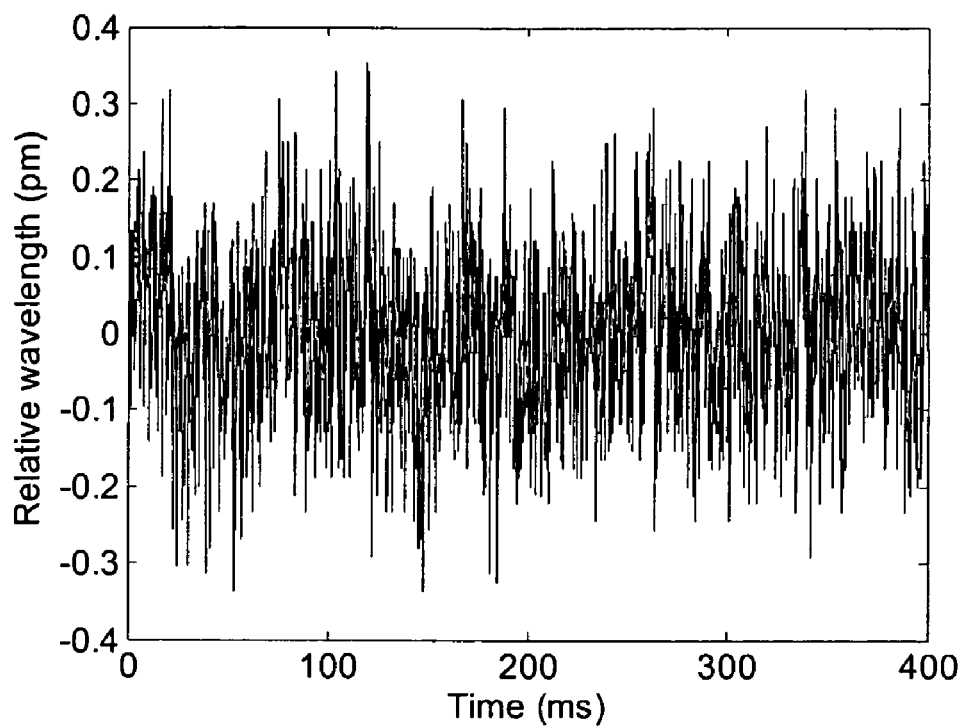
FIG. 4 is a plot of a noise response of the position-sensitive device (PSD), in embodiments of the disclosure.

For processing the output from a position-sensitive device (PSD) as described above, an analog to digital conversion can be used along with a scaling of an output voltage to complete the measurement of the centroid wavelengths $\lambda_i$ of the interrogating beams 14. A data acquisition (DAQ) board (PCI-62 59), for example, from National Instruments Corporation, Austin, Tex., can be used for this processing at a sampling rate of 1.25 million samples per second (MS/s) with a sixteen-bit digital resolution. FIG. 3 shows the nearly linear relationship between the output voltage of a position-sensitive device (PSD) and the centroid wavelength $\lambda_i$ of the interrogating beams 14. The stability of the analog voltage output from the position-sensitive device (PSD) as a measure of the centroid wavelength $\lambda_i$ is apparent from FIG. 4 in which noise within the converted centroid wavelength $\lambda_i$ is plotted over time, and highlights the precision available to these wavelength measurements. A root mean squared (rms) noise of 0.08 millivolts (mV), which is only slightly larger than the shot noise limit, corresponds of a 0.1 pm measurement precision at a sampling rate of 5 kHz.

Figure 5:
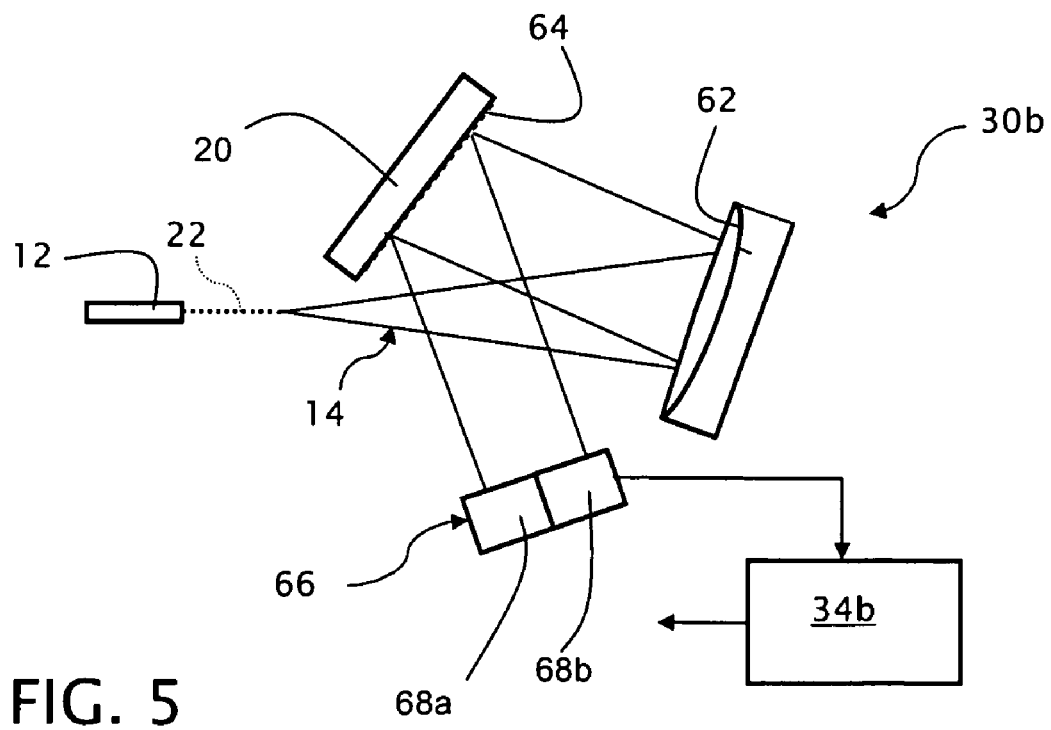
FIG. 5 is a block diagram of an alternative wavelength-tracking device in the swept wavelength interrogation system, in embodiments of the disclosure.

An alternative wavelength-tracking device 30b is depicted in FIG. 5. A front end of the wavelength tracking device 30b is similar to a front end of the wavelength tracking device 30a, including in combination the light source 12, a similar collimating optic 62, and a similar dispersive optic 64. However, the collimated but spectrally angularly dispersed light from the dispersive optic 64 is directly incident upon an alternative spatially sensitive detector 66. As shown, the detector 66 is a dual-element photodiode including respective photodiodes 68a and 68b. The collimated but spectrally angularly dispersed light of the light beam 14 is incident upon both photodiodes 68a and 68b, but through the space between the dispersive optic 64 and the two photodiodes 68a and 68b, the collimated beams are relatively spatially shifted in accordance with their wavelength content so that the light beam 14 is incident in different proportions upon the two photodiodes 68a and 68b. A normalized photocurrent difference between the two photodiodes 68a and 68b yields the relative position of the light beam 14, which can be calibrated into a measure of the centroid wavelengths $\lambda_i$ of the light beam 14. The output voltage V of the dual-element photodiode is expressed below as a relationship between photocurrents $I_1$ and $I_2$ collected from the photodiodes 68a and 68b and a distance L between the two photodiodes 68a and 68b:

$$V = \frac{(I_1 - I_2)}{(I_1 + I_2)} \cdot \frac{L}{2}$$

A processor 34b associated with the dual-element photodiode preferably includes an analog to digital converter and calibrator for registering the monitored voltage output of the dual-element photodiode as centroid wavelengths $\lambda_i$ of the light beam 14. The processor 34b can be implemented similar to the processor 34a for processing the analog output of the position-sensitive device (PSD).

While the disclosed position-sensitive device (PSD) of the wavelength-tracking device 30a is a simpler and less expensive alternative to the disclosed line-scan camera, the dual-element photodiode of the wavelength-tracking device 30b is a yet simpler and less expensive alternative to the position-sensitive device (PSD). The compact size, high-speed, and ability to accommodate higher optical power also recommends the dual-element photodiode as a spatially sensitive detector for wavelength-tracking systems in accordance with this invention.

Figure 6:
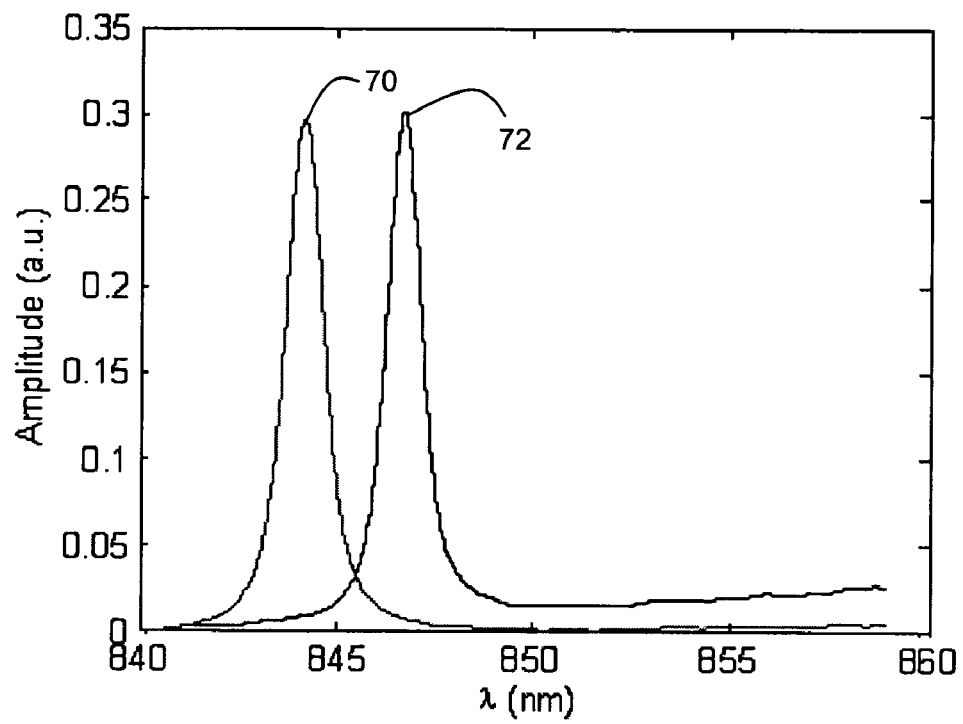
FIG. 6 plots resonance spectra measured in a two-channel reader for interrogating two resonant sensors exposed to different test conditions, in embodiments of the disclosure.
Figure 7:
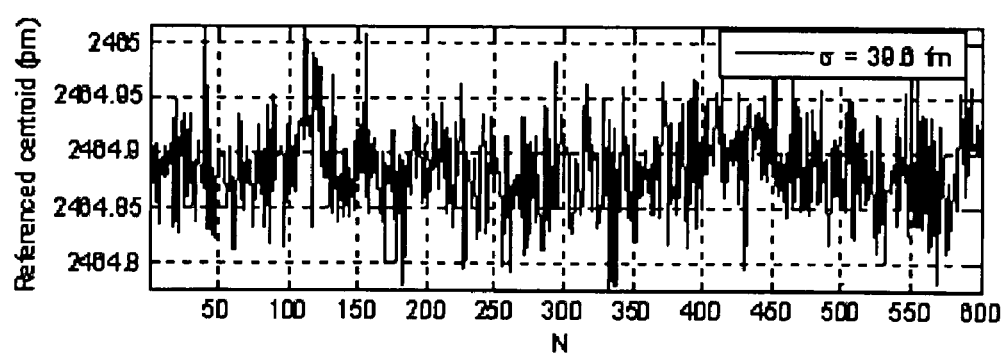
FIG. 7 plots baseline noise associated with centroid wavelength measurements of the resonant sensor responses, in embodiments of the disclosure.

FIGS. 6 and 7 depict an example of the expected performance of the swept wavelength interrogation system 10 in which two resonant sensors k1 and k2 are interrogated on separate channels using a position sensitive device (PSD) as described above for the wavelength-tracking device 30. One of the resonant sensors k1 is covered with water and the other resonant sensor k2 is covered by a 10 percent glycerol solution, which leads to a relative centroid wavelength shift from $\lambda_{k1}$ to $\lambda_{k2}$ of about 2.5 nm as shown in FIG. 6 between wavelength peaks 70 and 72. The baseline noise over a ten-minute period (i.e., 600 seconds) as shown in FIG. 7 is about 40 fm, which corresponds to an optical index change of about $5\times10^{-7}$ and exceeds the usual requirements for detecting small molecule kinetics assays. The noise contribution from the centroid wavelength $\lambda_i$ measurements of the light beam 14 accounts for only 10 fm. The majority of the 40 fm baseline noise is attributed to the measurement of sensor response.

While the spectral profiles of the light beam 14 are a more complex form than described by the measurement of the centroid wavelengths $\lambda_i$ alone, the centroid wavelengths $\lambda_i$ adequately capture the spectral power distribution of the interrogating beams 14 for the purpose of interrogating the resonant sensors 26 for their centroid wavelength $\lambda_k$ responses. However, the spectral profile of one portion of the light beam 14 monitored for its centroid wavelength $\lambda_i$ should match the spectral profile of the other portion of the light beam 14 used for interrogating the sensors 26, particularly with respect to any variations in the match over the tuning range.

Additional information gathered about the spectral profiles of the beam 14 can also be used to advantage when also capturing the spectral profiles of the resonant sensors by evaluating the sensor spectral profiles as convolution functions of the light beam spectral profiles. Preferably, the light source 12 is thermally stabilized so that the primary effect of the laser tuning is a wavelength shift in the spectral profile.

The disclosure has been described with reference to various specific embodiments and techniques. However, many variations and modifications are possible while remaining within the spirit and scope of the disclosure.

The invention claimed is:

1. A swept wavelength interrogation system comprising:
a tunable light source having a light beam tunable over a range of wavelengths;
an optical reader to distribute the light beam among a plurality of sensors and for measuring response spectra from the sensors; and
a wavelength-tracking device to measure centroid wavelengths of the light beam with a given precision,
the light beam having a linewidth that exceeds the given precision of the measured centroid wavelengths.

2. The system of claim 1 wherein the linewidth of the light beam exceeds the given precision of the measured centroid wavelengths by a factor of about 10 or more.

3. The system of claim 2 wherein the linewidth of the light beam is about 10 picometers or more and the given precision of the measured centroid wavelengths is less than about one picometer.

4. The system of claim 1 wherein the wavelengths of the light beam are spaced by a nominal step size and the linewidth of the light beam exceeds the nominal step size.

5. The system of claim 1 wherein the sensors have a resonance width and the linewidth of the light beam being greater than about five percent of the resonance width of the sensors.

6. The system of claim 5 wherein the linewidth of the light beam approaches the resonance width of the sensors.

7. The system of claim 1 wherein the tunable light source is a multi-longitudinal mode laser that simultaneously oscillates in a multitude of different longitudinal modes to enlarge the linewidth of the light beam.

8. The system of claim 7 wherein the multi-longitudinal mode laser simultaneously oscillates in about 100 or more longitudinal modes to reduce the influence of mode hopping.

9. The system of claim 1 further comprising a processor for determining centroid wavelengths of the sensor response spectra.

10. The system of claim 9 wherein the centroid wavelengths of the sensor response spectra have a measurement error $\sigma_c$ according to:

$$\sigma_c = \sqrt{\sigma_\lambda + \sigma_\gamma}$$

where $\sigma_\lambda$ is a measurement error of the centroid wavelengths of the light beam and $\sigma_\gamma$ is a measurement error of the response from the sensors.

11. The system of claim 10 wherein the measurement error $\sigma_c$ is about 100 femtometers or less, and the measurement error $\sigma_\lambda$ is about 0.3 picometers or less.

12. A wavelength tracking apparatus of a swept wavelength sensor interrogation system to measure a centroid wavelength of sensor resonance, comprising:
a dispersive optic that alters a spatial position of a light beam as a function of the beam's wavelength;
a sensor that measures optical power as a function of the spatial position of the light beam, and
a processor that converts the measured optical power to a measure of the centroid wavelength of the light beam, and the measured centroid wavelength being used to calculate the centroid wavelength ($C_k$) of the sensor resonance.

13. The apparatus of claim 12 wherein the centroid wavelength of sensor resonance is based on the centroid wavelengths of the light beam and the energy contents of the light beam returning from the sensor.

14. The apparatus of claim 12 wherein both the centroid wavelengths of the light beam and the centroid wavelength of sensor resonance represent a weighted mean of a plurality of wavelengths weighted according to the optical energy content of the wavelengths.

15. The apparatus of claim 12 wherein the wavelengths for determining the centroid wavelength of sensor resonance are the measured centroid wavelengths of the light beam.

16. The apparatus of claim 12 wherein the light beam has a linewidth of at least 10 picometers, and the sensor system is arranged for spatially distinguishing among the centroid wavelengths of the light beam to a precision of less than about 1 picometer.

17. A method of interrogating an array of sensors to measure a response to an analyte proximate to the sensor, comprising:
tuning a light source to provide a light beam having a range of wavelengths,
splitting the light beam to a beam-monitoring pathway and a sensor-interrogating pathway,
measuring centroid wavelengths of the light beam along the beam-monitoring pathway,
distributing optical power of the light beam among the array of sensors along the sensor-interrogating pathway,
measuring optical power returning from the array of sensors, and
determining centroid wavelengths of response spectra from the sensors based on the measured centroid wavelengths of the light beam and on the measured optical power returning from the array of sensors.

18. The method of claim 17 wherein both the centroid wavelengths of the light beam and the centroid wavelengths of the response spectra from the sensors represent a weighted mean of a plurality of considered wavelengths weighted according to optical energy content of the considered wavelengths.

19. The method of claim 17 wherein the centroid wavelengths of the light beam are measured with a given precision and the light beam has a linewidth that exceeds the given precision with which the centroid wavelengths of the light beam are measured.

20. The method of claim 17 wherein tuning includes outputting the light beam as multi-longitudinal mode beam containing at least 100 different longitudinal modes that vary in modal content over the range of wavelengths of the light beam.

21. The method of claim 17 wherein the measuring includes
    altering a spatial position of the light beam as a function of the wavelength of the light beam,
    measuring optical power in reference to the spatial position of the light beam, and
    converting the optical power measured in reference to the spatial position of the light beam into a measure of the centroid wavelength of the light beam.

* * * * *